US010835626B2

(12) United States Patent
Yadav et al.

(10) Patent No.: US 10,835,626 B2
(45) Date of Patent: Nov. 17, 2020

(54) SYSTEMS AND METHODS FOR COMBINED HIGH INTENSITY NARROW SPECTRUM AND NON-HIGH INTENSITY NARROW SPECTRUM LIGHTING FOR SURFACE DISINFECTION IN VARIABLY OCCUPIED ENVIRONMENTS

(71) Applicant: Hubbell Incorporated, Shelton, CT (US)

(72) Inventors: Pritam Yadav, Greenville, SC (US); Thomas James Veltri, Simpsonville, SC (US)

(73) Assignee: Hubbell Incorporated, Shelton, CT (US)

( * ) Notice: Subject to any disclaimer, the term of this patent is extended or adjusted under 35 U.S.C. 154(b) by 233 days.

(21) Appl. No.: 15/797,287

(22) Filed: Oct. 30, 2017

(65) Prior Publication Data
US 2018/0117189 A1 May 3, 2018

Related U.S. Application Data

(60) Provisional application No. 62/415,004, filed on Oct. 31, 2016.

(51) Int. Cl.
| *A61L 2/08* | (2006.01) |
| *A61L 2/24* | (2006.01) |
| *A61N 5/06* | (2006.01) |
| *A61L 9/20* | (2006.01) |

(52) U.S. Cl.
CPC .............. *A61L 2/084* (2013.01); *A61L 2/24* (2013.01); *A61L 9/20* (2013.01); *A61N 5/0613* (2013.01); *A61L 2202/14* (2013.01)

(58) Field of Classification Search
CPC ... A61L 2/084; A61L 2/24; A61L 9/20; A61L 2202/14; A61N 5/0613
See application file for complete search history.

(56) References Cited

U.S. PATENT DOCUMENTS

| 9,572,901 | B2* | 2/2017 | Todeschini | ............ | A61L 2/0052 |
| 10,372,952 | B2* | 8/2019 | Todeschini | ........... | G06K 7/1413 |
| 2017/0028214 | A1* | 2/2017 | Stasko | ................. | A61N 5/0603 |
| 2017/0028215 | A1* | 2/2017 | Medendorp, Jr. | ..... | A61N 5/0603 |
| 2017/0147843 | A1* | 5/2017 | Todeschini | ............ | A61L 2/0052 |
| 2017/0246329 | A1* | 8/2017 | Lloyd | ....................... | A61L 2/10 |
| 2018/0320872 | A1* | 11/2018 | Weeks, Jr. | ................ | F21S 8/03 |

* cited by examiner

*Primary Examiner* — Regina M Yoo
(74) *Attorney, Agent, or Firm* — Michael Best & Friedrich, LLP

(57) ABSTRACT

Systems and methods for combined HINS and non-HINS lighting for surface disinfection. A lighting system controller is provided, which includes a memory, an i/o interface, and an electronic processor. The processor is configured to retrieve from the memory at least one characteristic of an area to be disinfected; determine, based on a signal received from a first sensor positioned to sense the presence of a person in the area, whether a person is present in the area; and, when a person is present in the area, determine a first drive signal based on the at least one characteristic and the presence of the person, and a second drive signal based on the presence of the person in the area and the first drive signal. The processor provides the first drive signal to drive to a HINS LED array and the second drive signal to drive a non-HINS LED array.

20 Claims, 3 Drawing Sheets

SYSTEMS AND METHODS FOR COMBINED HIGH INTENSITY NARROW SPECTRUM AND NON-HIGH INTENSITY NARROW SPECTRUM LIGHTING FOR SURFACE DISINFECTION IN VARIABLY OCCUPIED ENVIRONMENTS

RELATED APPLICATION

The present application claims the benefit of U.S. Provisional Patent Application No. 62/415,004, filed Oct. 31, 2016, the entire contents of which is hereby incorporated by reference.

FIELD

The present application relates to the field of lighting and lighting control systems.

BACKGROUND

High Intensity Narrow Spectrum (HINS) lighting systems include light devices, such as light-emitting diodes (LEDs) configured to output light at wavelengths from approximately 400 nm to approximately 420 nm (for example, 405 nm). Light at such wavelengths has been shown to inactivate (that is, kill or damage) bacteria, including medically significant bacteria, such as Methicillin-resistant *Staphylococcus aureus* (MRSA). Accordingly, HINS lights may be used to disinfect surfaces in, for example, medical facilities, food storage or preparation facilities, environmentally controlled storage facilities, and in any other areas where it is desirable to control the occurrence of bacteria. Effective disinfection requires a sufficient dose of HINS light to be delivered within a particular duration.

DETAILED DESCRIPTION

Figure 1:
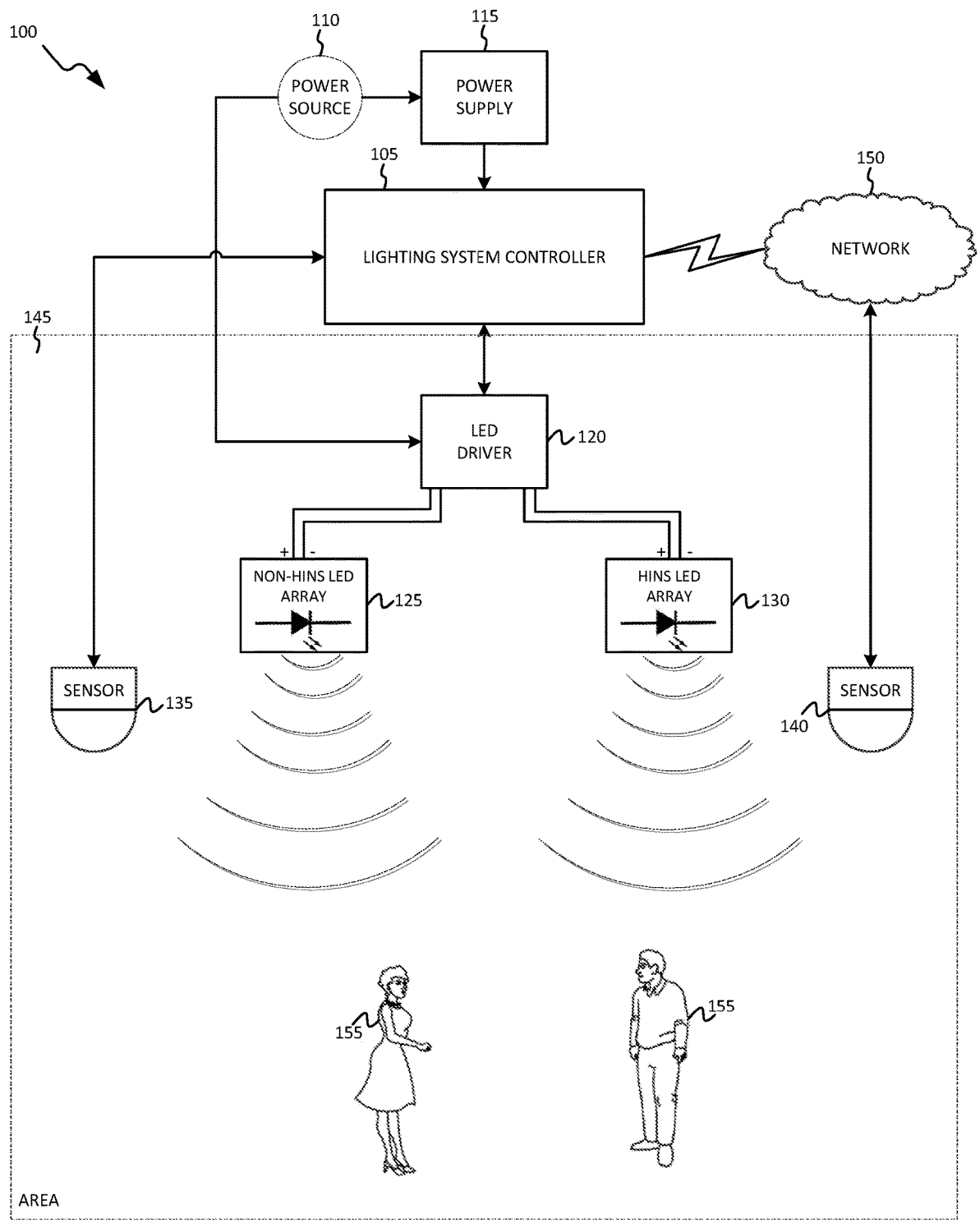
FIG. 1 is a block diagram of a lighting system, according to some embodiments.

It is desirable to control the occurrence of potentially harmful bacteria in certain locations, for example, medical facilities, food storage or preparation facilities, environmentally controlled storage facilities, and the like. In such locations, HINS lighting systems may be used for surface disinfection. Effective disinfection using HINS light requires delivery of a sufficient dose (that is, sufficient energy) of light, measured in joules per square centimeter ($J/cm^2$). The dose of energy delivered to a surface (and thus to the bacteria on the surface) depends on the intensity of the HINS light and the duration that the light is applied to the surface. Accordingly, energy dosage may be varied by varying the intensity and duration of the HINS light applied in an area. Some applications (for example, food processing) may require greater dosages than other applications (for example, disinfection of surfaces in an office environment).

Using conventional systems, it may not always be possible or desirable to produce HINS light at the recommended intensity for the recommended duration based on the application or the environment. For example, when an area is unoccupied, HINS light may be used at the recommended intensity for the recommended duration to achieve effective disinfection. However, HINS light is in the near-ultraviolet spectrum, and is visible to humans as a blue or purple light. When an area is occupied by humans, HINS light may not provide sufficient visibility and the shade or intensity of the light may be visually uncomfortable (for example, by altering the appearance of objects and surroundings in the illuminated area).

Accordingly, embodiments provide systems and methods for combined high intensity narrow spectrum and non-high intensity narrow spectrum lighting for surface disinfection in variably occupied environments.

One example embodiment provides a lighting system. The system provides a driver configured to provide a first drive signal and a second drive signal, a high intensity narrow spectrum (HINS) LED array configured to receive the first drive signal, a non-HINS LED array configured to receive the second drive signal, a first sensor positioned to sense the presence of a person in the area, and an electronic controller, which is coupled to the driver and the first sensor. The electronic controller includes a memory and an electronic processor. The electronic processor is configured to retrieve from the memory at least one characteristic of the area. The electronic processor is configured to determine, via the first sensor, whether a person is present in the area. The electronic processor is configured to, when a person is present in the area, determine the first drive signal based on the at least one characteristic and the presence of the person; determine the second drive signal based on the presence of the person in the area and the first drive signal; control the driver to provide the first drive signal to the HINS LED array; and control the driver to provide the second signal to the non-HINS LED array.

Another example embodiment includes a method of controlling a lighting system for surface disinfection in an area. The method includes retrieving, with an electronic processor from a memory coupled to the electronic processor, at least one characteristic of the area. The method includes determining, via a first sensor positioned to sense the presence of a person in the area, whether a person is present in the area. The method includes, when a person is present in the area, determining a first drive signal for a driver coupled to the electronic processor based on the at least one characteristic and the presence of the person. The method includes, when a person is present in the area, determining a second drive signal based on the presence of the person in the area and the first drive signal. The method includes, when a person is present in the area, controlling the driver to provide the first drive signal to a high intensity narrow spectrum (HINS) LED array. The method includes, when a person is present in the area, controlling the driver to provide the second signal to a non-HINS LED array.

Yet another example embodiment provides a lighting system controller. The controller includes a memory, an input/output interface, and an electronic processor. The electronic processor is coupled to the memory and the input/output interface. The electronic processor is configured to retrieve from the memory at least one characteristic of an area to be disinfected. The electronic processor is configured to determine, based on a signal received via the input/output interface from a first sensor positioned to sense the presence of a person in the area, whether a person is present in the area. The electronic processor is configured to, when a person is present in the area, determine a first drive signal based on the at least one characteristic and the presence of the person. The electronic processor is configured to determine a second drive signal based on the presence of the person in the area and the first drive signal. The electronic processor is configured to provide, via the input/output interface, the first drive signal to a driver to drive to a HINS LED array. The electronic processor is configured to provide, via the input/output interface, the second drive signal to the driver to drive a non-HINS LED array.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting, and coupling. Further, "connected" and "coupled" are not restricted to physical or mechanical connections or couplings, and can include electrical connections or couplings, whether direct or indirect. Also, electronic communications and notifications may be performed using any known means including wired connections, wireless connections, etc.

It should also be noted that a plurality of hardware and software based devices, as well as a plurality of different structural components may be used to implement the invention. In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the invention may be implemented in software (e.g., stored on non-transitory computer-readable medium) executable by one or more processors. As such, it should be noted that a plurality of hardware and software based devices, as well as a plurality of different structural components may be utilized to implement the invention. For example, "control units" and "controllers" described in the specification can include one or more processors, one or more memory modules including non-transitory computer-readable medium, one or more input/output interfaces, and various connections (e.g., a system bus) connecting the components.

For ease of description, some or all of the exemplary systems presented herein are illustrated with a single exemplar of each of its component parts. Some examples may not describe or illustrate all components of the systems. Other exemplary embodiments may include more or fewer of each of the illustrated components, may combine some components, or may include additional or alternative components.

FIG. 1 illustrates an exemplary embodiment of a lighting system 100. The system 100 includes a lighting system controller 105, a power source 110, a power supply 115, a driver 120, a non-HINS LED array 125, a HINS LED array 130, a first sensor 135, and a second sensor 140. The lighting system controller 105, the power source 110, the power supply 115, the driver 120, the non-HINS LED array 125, the HINS LED array 130, the first sensor 135, and the second sensor 140, as well as various other modules (not shown), are coupled directly, by one or more control or data buses that enable communication therebetween.

The lighting system controller 105, described more particularly below (with respect to FIG. 2), controls the driver 120, the non-HINS LED array 125, and the HINS LED array 130 to produce HINS and non-HINS (for example, warm white) light in the area 145. The area 145 may be any area, within which it is desirable to control the occurrence of bacteria. For example, and without limitation, the area 145 may be a medical facility, a food storage or preparation facility, an environmentally controlled storage facility, and the like. The area 145 may also be any other space where it is feasible to control the occurrence of bacteria on surfaces using HINS light.

The power source 110 and the power supply 115 supply a nominal power to the controller 105. In some embodiments, the power supply 115 receives an alternating-current (AC) power from the power source 110 and converts the AC power into a nominal direct-current (DC) power. In some embodiments, the power source 110 may supply an AC power having approximately 100V to approximately 120V at a frequency of approximately 50 Hz to approximately 60 Hz. In other embodiments, the power source 110 supplies an AC power having approximately 200V to approximately 240V at a frequency of approximately 50 Hz to approximately 60 Hz. In other embodiments, the power supply 115 includes a battery, or other power storage device.

The driver 120 receives AC power from the power source 110 and produces an output drive signal (for example, a constant direct current (DC) at a specific voltage) to each of the non-HINS LED array 125 and the HINS LED array 130. In some embodiments, the driver 120 is configured to receive DC power from the power supply 115. Regardless of its power source, the driver 120 receives a control signal from the controller 105, and in response to the control signal, the driver 120 independently varies the DC output drive signals to the non-HINS LED array 125 and the HINS LED array 130. This produces, within the area 145, non-HINS (for example, white) light of varying intensity and duration and HINS light of varying intensity and duration, either simultaneously or separately. Some embodiments include more than one driver 120. For example, some embodiments may include one driver for each array. In some embodiments, the driver includes a controller, which acts as a current splitter to divide current between the LED arrays (the non-HINS LED array 125 and the HINS LED array 130) based on control signals received from the lighting system controller 105. In other embodiments, the controller/current splitter may be external to the driver 120.

The non-HINS LED array 125 includes one or more light-emitting diodes (LEDs) operating to produce light in the visible spectrum. In one embodiment, the non-HINS LED array produces warm white light, (for example, at a color temperature of 3000K). In some embodiments, the non-HINS LED array 125 produces light at other colors and color temperatures. The LEDs and other components (for example, power circuitry, heat sinks, and the like) may be contained within a housing and may be part of a recessed ambient lighting system, a recessed down lighting system, a suspended direct lighting system, a suspended indirect lighting system, a track lighting system, an area lighting system, a flood lighting system, and the like. In some embodiments, the non-HINS LED array 125 may include an optic coupled to the LEDs. In such an embodiment, the optic may be a diffusion optic, a prismatic optic, a reflector optic, a total internal reflection (TIR) optic, a combination optic, a light pipe or edge lit optic, and the like.

The HINS LED array 130 includes one or more high intensity narrow spectrum LEDs operating with an output frequency of approximately 400 nm to approximately 420 nm. In one exemplary embodiment, the HINS LEDs have an output frequency of approximately 405 nm. The HINS LED array 130, like the non-HINS LED array 125 may be contained within a housing and may include optics, as described above. In some embodiments, the HINS LED array 130 may be collocated or combined with the non-HINS LED array 125 in a single housing. In other embodiments, multiple combined HINS/non-HINS LED arrays are deployed in one or more areas.

As noted above, the HINS LED array 130 may be used to disinfect surfaces within the area 145. Accordingly, the HINS LED array 130 is positioned such that it can illuminate all of the surfaces within the area 145 to be disinfected. The non-HINS LED array 125 is positioned such that it illuminates substantially the same portions of the area 145 as the HINS LED array 130. Some embodiments include two or more HINS LED arrays as needed to provide sufficient coverage, and thus, disinfection, of all of the surfaces in the area 145. In such embodiments, the system 100 includes sufficient non-HINS LED arrays arranged such that they illuminate substantially the same portions of the area 145 as the two or more HINS LED arrays. Whether there are one or many of each type of LED array, as described more particularly below, the controller 105 may use inputs from the first sensor 135, the second sensor 140, or both to control the driver 120 (or multiple drivers) to illuminate the area 145 with varying degrees of HINS light and non-HINS (for example, white) light.

The first sensor 135 and the second sensor 140 may be electronic or electromechanical devices (for example, transducers), which detect aspects of the environment of the area 145 and communicate those aspects as electrical signals to the controller 105. Either or both of the sensors may be a passive infrared (PIR) sensor, an ultrasonic sensor, a dual-tech sensor (that is, a combined infrared/ultrasonic sensor), a microwave sensor, an acoustic sensor, or a thermopile sensor. In some embodiments, one or both of the first sensor 135 and the second sensor 140 may capture images (for example, video, still images, or thermal images) of the area 145. Some sensors may combine two or more technologies. For example, a microwave sensor may be combined with a thermal imaging sensor to detect people who are moving or being still (for example, a person sleeping in a hospital bed). The first sensor 135 and the second sensor 140 are positioned and configured to sense the presence in the area 145 of, for example, one or more persons 155. The controller 105 receives the electrical signals, captured images, or both, and analyzes them to determine whether the area 145 is vacant or occupied. In some embodiments, the controller 105 executes an object classifier to detect objects (for example, one or more persons 155) in captured images.

The network 150 may a wired or wireless network. All or parts of the network 150 may be implemented using various existing networks, for example, a cellular network, the Internet, a Bluetooth™ network, a wired local area network (for example, Ethernet), a wireless local area network (for example, Wi-Fi), a wireless accessory Personal Area Network (PAN), and a public switched telephone network (PSTN). The network 150 may also include future-developed networks. As illustrated in FIG. 1, the lighting system controller 105 and the second sensor 140 communicate with each other using the network 150 using suitable wireless or wired communications protocols. In some embodiments, communications with other components of the system 100 (for example, the first sensor 135 and the driver 120) or other external devices (not shown) occurs over the network 150.

For ease of description, a single system 100 is illustrated providing light in a single area 145. This should not be considered limiting. Embodiments of the system 100 may provide light for multiple areas. In some embodiments, one lighting system controller 105 controls multiple drivers and LED arrays (for example, HINS arrays, non-HINS arrays, or combined HINS/non-HINS arrays) to provide light for multiple areas. In other embodiments, multiple lighting system controllers in communication with one and other (for example, over the network 150) provide light for multiple areas. In some embodiments, the area 145 is divided into two or more zones, each zone having a HINS LED array, a non-HINS LED array, and a sensor positioned to detect the presence of persons within the zone. In such embodiments, the lighting in the zones may be controlled independently of one another.

Figure 2:
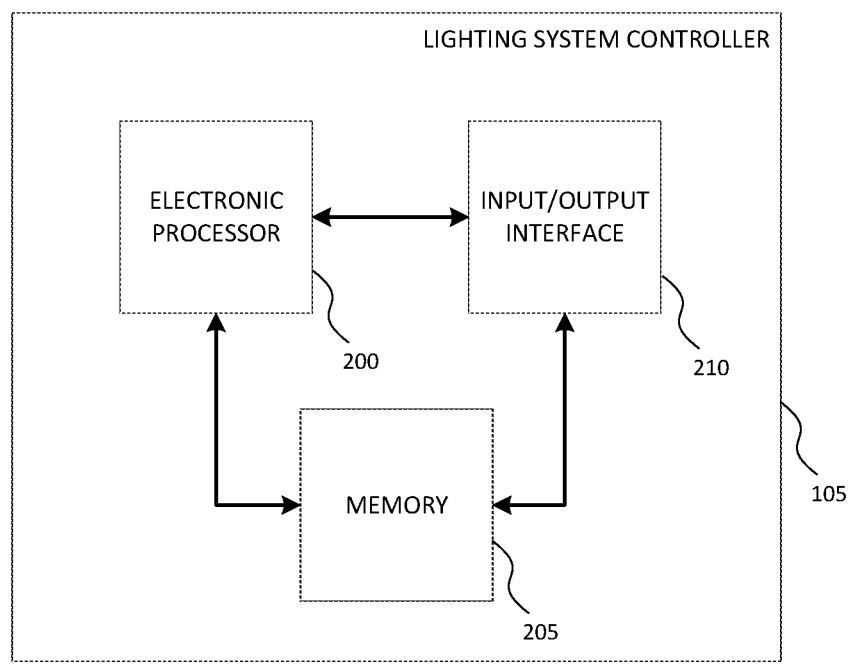
FIG. 2 is a block diagram of a lighting system controller, according to some embodiments.

FIG. 2 is a diagram of one exemplary embodiment of the lighting system controller 105. In the embodiment illustrated, the lighting system controller 105 includes an electronic processor 200 (for example, a microprocessor, or other electronic controller), a memory 205, and an input/output interface 210. The electronic processor 200, the memory 205, and the input/output interface 210, as well as the other various modules are coupled directly, by one or more control or data buses, or a combination thereof to enable communication therebetween. The memory 205 may include read-only memory (ROM), random access memory (RAM), other non-transitory computer-readable media, or a combination thereof. In some embodiments, the memory 205 stores information regarding the characteristics the environment of the area 145 (for example, the dimensions of the area 145, the use of the area 145, the types of bacteria likely to be found in the area 145, what types of bacteria it is desirable to protect against in the area 145, and when the area 145 is likely to be occupied or vacant). The memory 205 may also store information regarding the LED arrays (for example, the physical placement of the LED arrays within the area 145, the wavelength of the HINS LED array 130, and the color temperature of the non-HINS LED array 125). The memory 205 may also store information regarding the intensity and duration of HINS light required to accomplish effective disinfection of different types of bacteria. The electronic processor 200 is configured to retrieve instructions and data from the memory 205 and execute, among other things, instructions to perform the methods described herein.

The input/output interface 210 obtains information and signals from, and provides information and signals to, (for example, over one or more wired and/or wireless connections) devices both internal and external to the lighting system controller 105. In one example, the electronic processor 200 sends control signals to the driver 120 via the input/output interface 210. In another example, the electronic processor 200 communicates with the first sensor 135 via the input/output interface 210 using a wired connection. The input/output interface 210 may also include one or more network interfaces. For example, as illustrated in FIG. 2, the electronic processor 200 communicates, via the input/output interface 210, with the second sensor 140 via the network 150 over a wired or wireless network connection.

Figure 3:
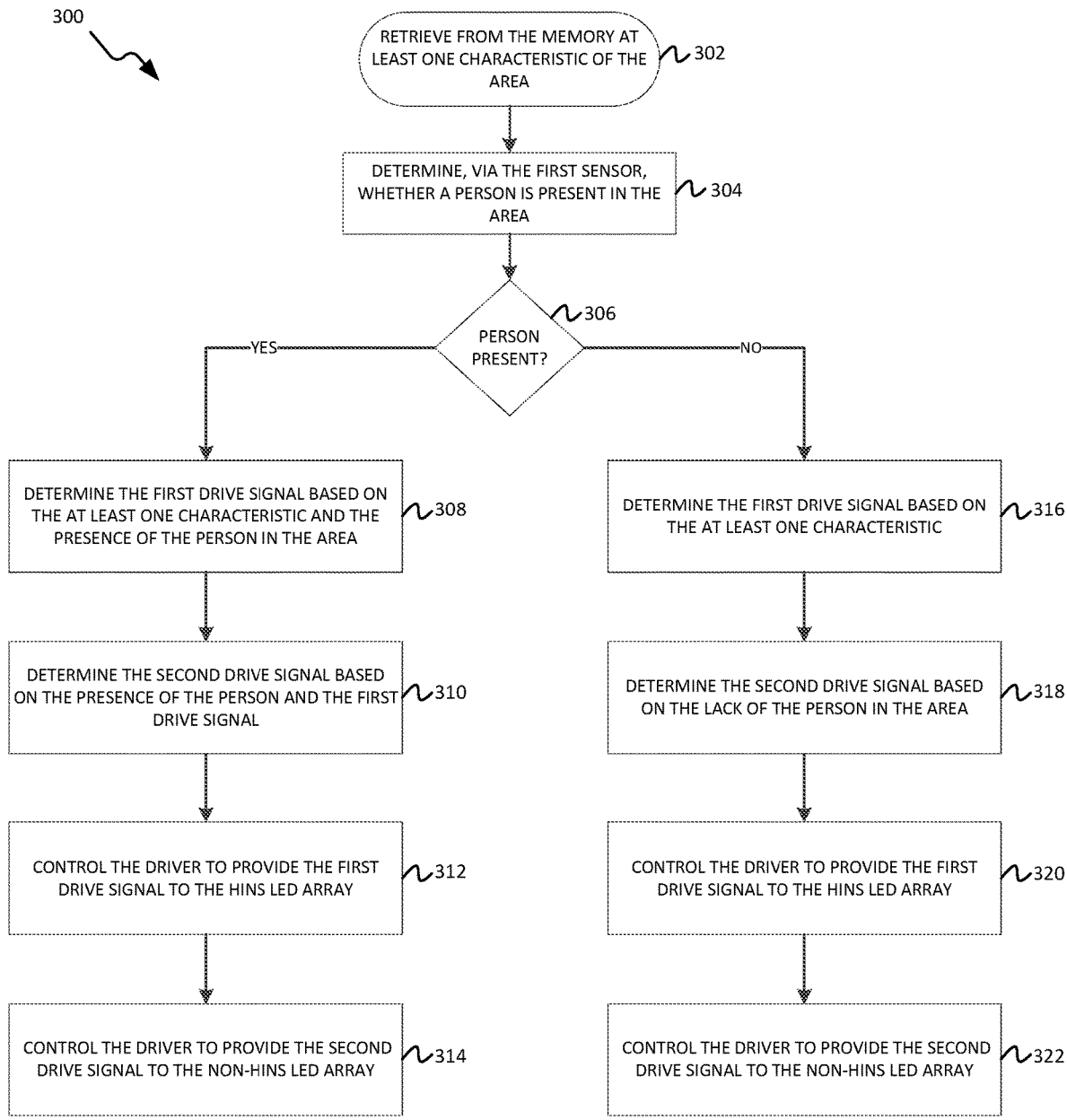
FIG. 3 is flow chart of a method for operating the lighting system of FIG. 1

As noted above, it may not always be possible or desirable to produce HINS light at the recommended intensity for the recommended duration when, for example, the area 145 is occupied. Accordingly, FIG. 3 illustrates an exemplary method 300 for operating the lighting system 100 to apply HINS light, non-HINS light, or both based on at least the occupancy or vacancy of the area. As an example, the method 300 is explained in terms of the lighting system 100 as illustrated in FIG. 1, with the non-HINS LED array 125 configured to produce white light.

At block 302, the electronic processor 200 retrieves from the memory 205 at least one characteristic of the area. The at least one characteristic may be, for example, one or more dimensions of the area, a use of the area 145 (for example, food preparation, food storage, office space, and the like), a type of bacteria, which it is desirable to control within the area, or some combination of the foregoing. At block 304, the electronic processor 200 determines, via the first sensor 135, whether a person 155 is present in the area 145. In some embodiments, the electronic processor 200 may determine whether a person is present by interpreting signals from a passive infrared sensor, an ultrasonic sensor, a dual-tech sensor, a microwave sensor, an acoustic sensor, a thermopile sensor. In some embodiments, the electronic processor 200 may determine whether a person is present by analyzing video or still images received from a thermal imaging sensor or an image capture device, such as a digital video camera. In some embodiments, the electronic processor 200 may determine whether a person is present via the first sensor 135 and the second sensor 140. For example, the electronic processor 200 may interpret signals from an acoustic sensor to be speech and may interpret temperature readings from a thermopile sensor as body heat from one or more persons 155. In another example the electronic processor 200 may interpret the signals from a microwave motion sensor to indicate that the area is vacant, while the signals from an infrared sensor indicate that the area 145 is indeed occupied by a person 155 not moving or not moving in the detectable area of the microwave sensors.

Regardless of what sensors are used, when the electronic processor 200 determines that a person 155 is present in the area 145, at block 306, the electronic processor 200 determines the first drive signal based on the at least one characteristic and the presence of the person 155, at block 308. The first drive signal is used to drive the HINS LED array 130 to produce HINS light. In one example, when the at least one characteristic is the type of bacteria to be damaged or killed, the electronic processor determines from this, and the operating frequency of the HINS LED array 130, an intensity and a duration of operation for the HINS LED array 130. The first drive signal is in turn based on the intensity and operating duration, and the presence of the person in the area 145. For example, because a person is present, the electronic processor 200 may reduce the intensity and increase the duration, to reduce the visual impact of the HINS light, while still delivering a sufficient dose of HINS light to achieve the desired level of disinfection. At block 310, the electronic processor 200 determines the second drive signal based on the presence of the person in the area and the first drive signal. The second drive signal includes an intensity and a duration for the white light. For example, because a person 155 is present in the area 145, more white light may be produced to improve visibility in the area 145 and mitigate the visual impact of the HINS light. The first drive signal is also used to determine the intensity and the duration of the non-HINS LED array 125, because, for example, the intensity of the HINS light may determine how much white light should be applied to effectively mitigate the visual discomfort caused by the HINS light. In some embodiments, a particular color range or color temperature range may be desirable for the area 145. In such embodiments, the second drive signal is determined based on the light color range or light color temperature range.

At block 312, the electronic processor 200 controls the driver 120 to provide the first drive signal to the HINS LED array 130. At block 314, the electronic processor 200 controls the driver 120 to provide the second signal to the non-HINS LED array 125. In some embodiments, the first and second control signals control a current splitter integrated with or external to the driver 120 to activate the non-HINS LED array 125 and the HINS LED array 130 to provide visually pleasing light in the area 145, which light still effectively disinfects the surfaces of the area 145.

Returning to block 306, when a person 155 is not present in the area 145, the electronic processor 200 determines the first drive signal based on the at least one characteristic, at block 316. With regard a type of bacteria, the first drive signal is determined as described with respect to block 308 above, except that the signal is not adjusted based on the presence of a person. At block 318, the electronic processor 200 determines the second drive signal based on the lack of a person 155 in the area 145 (that is, the sensor signals do not indicate that a person 155 is present in the area 145). In some cases, sensor signals indicating the lack of a person 155 may result in the electronic processor 200 determining a second drive signal that results in no white light being generated.

At block 320, the electronic processor 200 controls the driver 120 to provide the first drive signal to the HINS LED array 130. At block 322, the electronic processor 200 controls the driver to provide the second signal to the non-HINS LED array 125. In some embodiments, the first and second control signals control a current splitter in the driver 120 to activate only the HINS LED array 130, while leaving the non-HINS LED array 125 inactive, to provide a sufficient dose of HINS light in the area 145, which HINS light effectively disinfects the surfaces of the area 145 without extending the duration past what is recommended based on the type of bacteria.

Thus, the invention provides, among other things, systems and methods for combined high intensity narrow spectrum and non-HINS lighting for surface disinfection in variably occupied environments.

What is claimed is:
1. A lighting system for surface disinfection in an area, the lighting system comprising:
   a driver configured to provide a first drive signal and a second drive signal;
   a high intensity narrow spectrum (HINS) LED array configured to receive the first drive signal;
   a non-HINS LED array configured to receive the second drive signal;
   a first sensor positioned to sense the presence of a person in the area; and
   an electronic controller, coupled to the driver and the first sensor, including a memory and an electronic processor configured to
      retrieve from the memory at least one characteristic of the area;
      determine, via the first sensor, whether a person is present in the area; and
      when a person is present in the area,
         determine the first drive signal based on the at least one characteristic and the presence of the person;

determine the second drive signal based on the presence of the person in the area and the first drive signal;
control the driver to provide the first drive signal to the HINS LED array; and
control the driver to provide the second drive signal to the non-HINS LED array.

2. The lighting system of claim 1, wherein the electronic processor is further configured to, when a person is not present in the area,
determine the first drive signal based on the at least one characteristic;
determine the second drive signal based on the lack of a person in the area;
control the driver to provide the first drive signal to the HINS LED array; and
control the driver to provide the second drive signal to the non-HINS LED array.

3. The lighting system of claim 1, wherein the first drive signal includes an intensity and a duration of operation.

4. The lighting system of claim 1, wherein the electronic processor is further configured to determine the first drive signal based on an operating frequency of the HINS LED array.

5. The lighting system of claim 1, wherein the electronic processor is further configured to determine the second drive signal based on the first drive signal and a desired light color range for the area.

6. The lighting system of claim 1, wherein the at least one characteristic is at least one selected from a group consisting of at least one dimension of the area, a use of the area, and a type of bacteria.

7. The lighting system of claim 1, wherein the first sensor includes at least one of a group consisting of a passive infrared sensor, an ultrasonic sensor, a dual-tech sensor, a microwave sensor, an acoustic sensor, a thermopile sensor, a thermal imaging sensor, and an image capture device.

8. The lighting system of claim 1, further comprising:
a second sensor positioned to sense the presence of a person in the area;
wherein the electronic controller is coupled to the second sensor, and the electronic processor is further configured to
determine, via the first sensor and the second sensor, whether a person is present in the area.

9. A lighting system controller, the lighting system controller comprising:
a memory;
an input/output interface; and
an electronic processor, coupled to the memory and the input/output interface, wherein the electronic processor is configured to
retrieve from the memory at least one characteristic of an area to be disinfected;
determine, based on a signal received via the input/output interface from a first sensor positioned to sense the presence of a person in the area, whether a person is present in the area; and
when a person is present in the area,
determine a first drive signal based on the at least one characteristic and the presence of the person;
determine a second drive signal based on the presence of the person in the area and the first drive signal;
provide, via the input/output interface, the first drive signal to a driver to drive to a HINS LED array; and
provide, via the input/output interface, the second drive signal to the driver to drive a non-HINS LED array.

10. The lighting system controller of claim 9, wherein the electronic processor is further configured to, when a person is not present in the area,
determine the first drive signal based on the at least one characteristic;
determine the second drive signal based on the lack of a person in the area;
provide, via the input/output interface, the first drive signal to a driver to drive to a HINS LED array; and
provide, via the input/output interface, the second drive signal to the driver to drive a non-HINS LED array.

11. The lighting system controller of claim 9, wherein the electronic processor is further configured to determine the first drive signal based on an operating frequency of the HINS LED array.

12. The lighting system controller of claim 9, wherein the electronic processor is further configured to determine the second drive signal based on the first drive signal and a desired light color range for the area.

13. A method of controlling a lighting system for surface disinfection in an area, the method comprising:
retrieving, with an electronic processor from a memory coupled to the electronic processor, at least one characteristic of the area;
determining, via a first sensor positioned to sense the presence of a person in the area, whether a person is present in the area; and
when a person is present in the area,
determining a first drive signal for a driver coupled to the electronic processor based on the at least one characteristic and the presence of the person;
determining a second drive signal based on the presence of the person in the area and the first drive signal;
controlling the driver to provide the first drive signal to a high intensity narrow spectrum (HINS) LED array; and
controlling the driver to provide the second drive signal to a non-HINS LED array.

14. The method of claim 13, further comprising:
when a person is not present in the area,
determining the first drive signal based on the at least one characteristic;
determining the second drive signal based on the lack of a person in the area;
controlling the driver to provide the first drive signal to the HINS LED array; and
controlling the driver to provide the second drive signal to the non-HINS LED array.

15. The method of claim 13, wherein determining the first drive signal includes determining an intensity and a duration of operation.

16. The method of claim 13, wherein determining the first drive signal includes determining the first drive signal based on an operating frequency of the HINS LED array.

17. The method of claim 13, wherein determining the second drive signal includes determining the second drive signal based on the first drive signal and a desired light color range for the area.

18. The method of claim 13, wherein determining the first drive signal based on the at least one characteristic includes determining the first drive signal based on at least one selected from a group consisting of at least one dimension of the area, a use of the area, and a type of bacteria.

19. The method of claim 13, wherein determining whether a person is present in the area via the first sensor includes determining whether a person is present in the area via at least one of a group consisting of a passive infrared sensor, an ultrasonic sensor, a dual-tech sensor, a microwave sensor, an acoustic sensor, a thermopile sensor, a thermal imaging sensor, and an image capture device.

20. The method of claim 13, further comprising:
  determining, via the first sensor and a second sensor positioned to sense the presence of a person in the area, whether a person is present in the area.

* * * * *